United States Patent
Liu et al.

(10) Patent No.: US 9,856,518 B2
(45) Date of Patent: Jan. 2, 2018

(54) METHOD AND APPARATUS FOR A NANOPIPETTE BIOSENSOR

(71) Applicant: University of Notre Dame du Lac, Notre Dame, IN (US)

(72) Inventors: Shoupeng Liu, Mishawaka, IN (US); Satyajyoti Senapati, Mishawaka, IN (US); Yunshan Wang, South Bend, IN (US); Yu Yan, Mishawaka, IN (US); Hsueh-Chia Chang, Granger, IN (US)

(*) Notice: Subject to any disclaimer, the term of this patent is extended or adjusted under 35 U.S.C. 154(b) by 0 days.

(21) Appl. No.: 14/283,713

(22) Filed: May 21, 2014

(65) Prior Publication Data
US 2014/0349287 A1    Nov. 27, 2014

Related U.S. Application Data

(60) Provisional application No. 61/826,469, filed on May 22, 2013.

(51) Int. Cl.
    *C12Q 1/68* (2006.01)
(52) U.S. Cl.
    CPC ......... *C12Q 1/6816* (2013.01); *C12Q 1/6825* (2013.01)
(58) Field of Classification Search
    CPC ...... C12Q 1/68; C12Q 1/6816; C12Q 1/6825; C07H 21/02
    See application file for complete search history.

(56) References Cited

U.S. PATENT DOCUMENTS

| 6,361,944 B1* | 3/2002 | Mirkin et al. ............... 435/6.11 |
| 6,538,801 B2* | 3/2003 | Jacobson ................... B41J 2/01 345/107 |
| 8,083,926 B2 | 12/2011 | Chen |
| 8,518,227 B2 | 8/2013 | Qian |
| 8,546,168 B2 | 10/2013 | Sauer |
| 2005/0260119 A1 | 11/2005 | Sunkara |

(Continued)

FOREIGN PATENT DOCUMENTS

| WO | 2012051451 | 4/2012 |
| WO | WO 2014/149071 | * 3/2013 |

OTHER PUBLICATIONS

Tu et al, Fluorescence quenching of gold nanoparticles integrating with a conformation-switched hairpin oligonucleotide probe for microRNA detection, 2012, Chem. Commun., 48, 10718-10720.*

(Continued)

*Primary Examiner* — Narayan Bhat
(74) *Attorney, Agent, or Firm* — Notre Dame Intellectual Property Clinic

(57) ABSTRACT

A nanopipette biosensor capable of detecting a small concentration of target molecules within a sample solution using optical detection methods. The biosensor includes a nanopipette that connects a nanocolloid reservoir containing a nanocolloid solution and a sample reservoir containing a sample solution, where the nanopipette is tapered at the end connected to the sample reservoir. The nanocolloid solution includes nanoparticles functionalized with probes specific to miRNA of the target molecules and reporters. During the detection process, the nanocolloids nanoparticles aggregate such that plasmonic hotspots are formed. These hotspots magnify the reporter signals produced when the probes hybridize with target molecules.

20 Claims, 7 Drawing Sheets

(56) References Cited

U.S. PATENT DOCUMENTS

| | | | |
|---|---|---|---|
| 2009/0214392 A1* | 8/2009 | Kameoka et al. | ............ 422/102 |
| 2010/0072080 A1 | 3/2010 | Karhanek | |
| 2010/0297686 A1 | 11/2010 | Gogotsi | |
| 2012/0193659 A1 | 8/2012 | Andrews | |
| 2012/0222958 A1 | 9/2012 | Pourmand | |
| 2013/0189793 A1 | 7/2013 | Qian | |
| 2013/0337486 A1 | 12/2013 | Levchenko | |

OTHER PUBLICATIONS

Piper et al, A Renewable Nanosensor Based on a Glass Nanopipette, JACS, 2006, 128, 16462-16463.*

Piper et al, A Renewable Nanosensor Based on a Glass Nanopipette, JACS, 2006, 128, 16462-16463, Supporting information, pp. 1-6.*

Morris et al, Applications of nanopipettes in the analytical sciences, 2010, Analyst, 135, 2190-2202.*

Liu et al, Plasmonic hotspots of dynamically assembled nanoparticles in nanocapillaries: Towards a micro ribonucleic acid profiling platform, Biomicrofluidics 7, 061102, pp. 1-4. (Year: 2013).*

Nicholas A. Bell, Vivek V. Thacker, Silvia Hernandez-Ainsa, Maria E. Fuentes-Perez, Fernando Moreno-Herrero, Tim Liedl, Ulrich F. Keyser, Multiplexed ionic current sensing with class nanopores, Lab on a Chip, 2013, 1859-1862, 13-10.

Wenhong Li, Nicholas A. W. Bell, Silvia Hernandex-Ainsa, Vivek V. Thacker, Alana M. Thackray, Raymond Bujdoso, Ulrich F. Keyser, Single Protein Molecule Detection by Glass Nanopores, ACS Nano, 2013, 4129-4134, 7-5.

Bala Murali Venkatesan, Rashid Bashir, Nanopore sensors for nucleic acid analysis, Nature Nanotechnology, 2011, 615-624, 6-10.

Ronghui Zhou, Hsueh-Chia Chang, Vladimir Protasenko, Masaru Kuno, Amol Kumar Singh, Debdeep Jena, Huili (Grace) Xing, CdSe nanowires with illumination-enhanced conductivity: Induced dipoles, dielectrophoretic assembly, and field-sensitive emission, Journal of Applied Physics, 2007, 073704-1-073704-9, 101.

* cited by examiner

METHOD AND APPARATUS FOR A NANOPIPETTE BIOSENSOR

CROSS-REFERENCE TO RELATED APPLICATIONS

This application claims priority from U.S. Provisional Patent Application No. 61/826,469, filed on May 22, 2013, and PCT Application No. PCT/US14/38829, filed on May 20, 2014, which are hereby incorporated by reference in their entirety.

INCORPORATION-BY-REFERENCE OF MATERIAL SUBMITTED AS TEXT FILE VIA THE OFFICE ELECTRONIC FILING SYSTEM (EFS-WEB)

The Sequence Listing, which is part of the present disclosure, includes a computer readable form comprising nucleotide and/or amino acid sequences. The information recorded in computer readable form is identical to the written sequence listing. The subject matter of the Sequence Listing is incorporated herein by reference in its entirety.

BACKGROUND

Generally, early detection of serious diseases such as cancers and cardiovascular diseases is crucial to patient outcome and potentially survival. Consequently, identification and detection of certain biomarkers indicative of the presence of disease has been an important area of research. For example, irregular expressions of microRNA sequences ("miRNA") are an early indicator of many conditions such as cancer and cardiovascular disease. Individual irregularities are associated with particular conditions and used to identify the particular condition. Early detection can enable doctors to identify the type of disease and design a treatment strategy based upon the type and progression of the disease. The ability to monitor such small-molecule biomarkers can also assist in tracking treatment effectiveness during the treatment program as well as monitoring for recurrence.

Currently, detection of these biomarkers is expensive and time consuming. A cost-effective, portable method and apparatus for detecting target molecules, such as biomarkers, would facilitate diagnosis and treatment of a variety of conditions. Home-use prescreening devices would be a particular application.

Current options for detecting miRNA biomarkers include plasmonic optical sensors. Such sensors either required high-intensity and expensive laser light sources or expensive optical sensors due to the weak coupling between low-intensity light and surface plasmonic waves of nanoparticles. Current nanofabrication technologies required to produce the sensors are expensive and do not lend themselves to low-cost large-volume production.

Inexpensive method and apparatus are therefore essential for commercial realization of diagnostic devices based on miRNA biomarker profiling.

BRIEF SUMMARY

The following presents a simplified summary to provide a basic understanding of some aspects of the claimed subject matter. This summary is not an extensive overview. It is not intended to either identify key or critical elements or to delineate the scope of the claimed subject matter. Its sole purpose is to present some concepts in a simplified form as a prelude to the more detailed description that is presented later.

The described apparatuses and methods relate to the field of detection of small molecules within a sample, such as testing the concentration of miRNA within a sample solution for the purposes of screening for diseases and conditions. The disclosed nanoparticle-nanopipette biosensor allows for the quick, low-cost quantification of particles within a given sample using optical detection methods. In embodiments of the biosensor the nanopipette connects two reservoirs, a base reservoir and a sample reservoir, each with its own electrode.

A solution of nanocolloids is deposited into the base reservoir, filling the nanopipette; a sample solution, containing the particles targeted for detection, referred to as target molecules, is placed in the sample reservoir. The nanocolloids are functionalized with probes specific to the miRNA. In embodiments, these probes are polynucleotide-probes complementary to the target miRNA. In particular, the probes can be conformation-switching hairpin probes with fluorescent or Raman reporters, which eliminates the need to label target molecules. When the probe is in the hairpin conformation, unbound to a target miRNA, the reporters are quenched by the metallic nanocolloids. When the hairpin releases upon target capture, the quenching action stops and binding between the probe and the target miRNA is detectable. Consequently, the reporters of the probes functionalized to the nanocolloids are activated by target capture.

In some embodiments, the target molecules are labeled with fluorescent, Raman, Quantum Dots or other reporters. In such cases, unlabeled polynucleotide probes can be used and the nanocolloids can then be both metallic and dielectric.

In embodiments, an electric current is applied to the biosensor via electrodes in the sample and base reservoir, driving the target molecules into the nanopipette for a duration depending on the sensitivity needed for detection. After the nanopipette is loaded, a reverse field is applied to the biosensor. This packs the nanoparticles, both the nanocolloid and the target molecules, inside the tip of the nanopipette. As a result, the nanoparticles combine, creating an aggregate of nanocolloids with the target molecules located at the contact points between the nanocolloids. As used herein, the term "contact point" indicates the portion of the nanocolloid that is proximate to an adjacent nanocolloid within the aggregate. By adjusting the original nanocolloid concentration, the number of nanocolloids within the aggregate can be tuned from 1 to 1 million, depending on how many captured targets are desired.

Alternatively, the probe-functionalized nanocolloids can be packed into an aggregate first, before the sample containing the target is passed through the aggregate and the nanopipette tip. Unlike other techniques, all molecules, including the target molecules, of the sample must transit through the nanocolloid aggregate at the tip of the nanopipette. There is hence a minimum of target loss—most targets will be captured.

Nanocolloids are selected such that they couple easily with light. For example, the nanocolloid particles can be spherical in nature. Since the nanocolloid particles are closely packed within the aggregate, the nanocolloids' plasmonic waves overlap, forming intense hotspots near the contact points of adjacent nanocolloid particles packed in the aggregate. These hotspots magnify signals of reporters detectable through various optical detection methods, and target molecules can be quantified by measuring the intensity of the reporters as magnified by the hotspots.

The plasmonic hotspots develop if the spacing of the contact points is within a certain range, between 4 nanometers and 20 nanometers. The spacing of the nanocolloid aggregate is adjusted to this range. In this technique, the electric field is capable of adjusting the spacing to its optimum value for any given aggregate to optimize the intensity of the plasmonic hotspot.

Embodiments include a method for detecting a target molecule in a sample solution, comprising providing a biosensor including a base reservoir, a sample reservoir and a nanopipette that connects the base reservoir and the sample reservoir, wherein the nanopipette includes a tapered tip end. The detection method includes adding a nanocolloid solution comprising functionalized nanoparticles to the base reservoir, wherein each of the functionalized nanoparticles comprises a nanocolloid nanoparticle, a probe complementary to the target molecule, and a reporter; loading the nanocolloid solution into the nanopipette; and adding the sample solution to the sample reservoir. Next, the method includes loading the sample solution into the nanopipette where the target molecule in the sample solution hybridizes to the probe of at least one of the functionalized nanoparticles, thereby activating the reporter; and assembling an aggregate of the functionalized nanoparticles, wherein the aggregate assembles proximate to the tip end of the nanopipette and the nanocolloid nanoparticles form a plasmonic hotspot. Finally, a signal produced by the activated reporter is observed using an optical detection technique enabled at least in part by intensification of the signal by the plasmonic hotspot.

The steps of loading the sample solution and forming the aggregate can be accomplished by applying a first voltage to the sample reservoir and the base reservoir, wherein a current from the first voltage drives the sample solution into the nanopipette; and applying a second voltage to the sample reservoir and the base reservoir, the second voltage having a reverse polarity from the first voltage, wherein the functionalized nanoparticles form the aggregate proximate to the tip end of the nanopipette based at least in part upon the application of the second voltage.

To the accomplishment of the foregoing and related ends, certain illustrative aspects of the claimed subject matter are described herein in connection with the following description and the annexed drawings. These aspects are indicative of various ways in which the subject matter may be practiced, all of which are intended to be within the scope of the claimed subject matter. Other advantages and novel features may become apparent from the following detailed description when considered in conjunction with the drawings.

BRIEF DESCRIPTION OF THE DRAWINGS

The systems, devices and methods may be better understood by referring to the following description in conjunction with the accompanying drawings, in which like numerals indicate like structural elements and features in various figures. The components in the figures are not necessarily to scale, and simply illustrate the principles of the systems, devices and methods. The accompanying drawings illustrate only possible embodiments of the systems, devices and methods and are therefore not to be considered limiting in scope.

DETAILED DESCRIPTION

Aspects of the system and methods are described below with reference to illustrative embodiments. The references to illustrative embodiments below are not made to limit the scope of the claimed subject matter. Instead, illustrative embodiments are used to aid in the description of various aspects of the systems and methods. The description, made by way of example and reference to illustrative reference is not meant to be limiting as regards any aspect of the claimed subject matter.

Disclosed herein are methods of detecting, diagnosing, monitoring or managing conditions in a subject. Detection of a biomarker in a sample can be indicative, or confirmatory, of a diagnosis of a condition. Monitoring can include detection or repeated detection of a biomarker from a sample or samples of a subject in which the biomarker has already been detected. Managing can include therapeutic intervention based upon the presence or absence of a biomarker in a subject. On the basis of the detection of the presence, absence or quantity of a biomarker in a subject, a treatment can be selected, monitored, or modified. Detection of the presence, absence or quantity of a biomarker in a subject can comprise detection of a biomarker in a sample from the subject.

The detection methods described herein are generally performed on a subject or on a sample from a subject. A sample can contain or be suspected of containing a biomarker. A sample can be a biological sample from a subject. The subject can be a subject having, diagnosed with, suspected of having, at risk for developing a condition, or even a subject without any indicia of the condition. The subject can be an animal subject, preferably a mammal and most preferably a human. A sample can be a blood sample, a serum sample, a plasma sample, a cerebrospinal fluid sample, or a solid tissue sample. A sample solution is formed with a sample from a subject.

Figure 1:
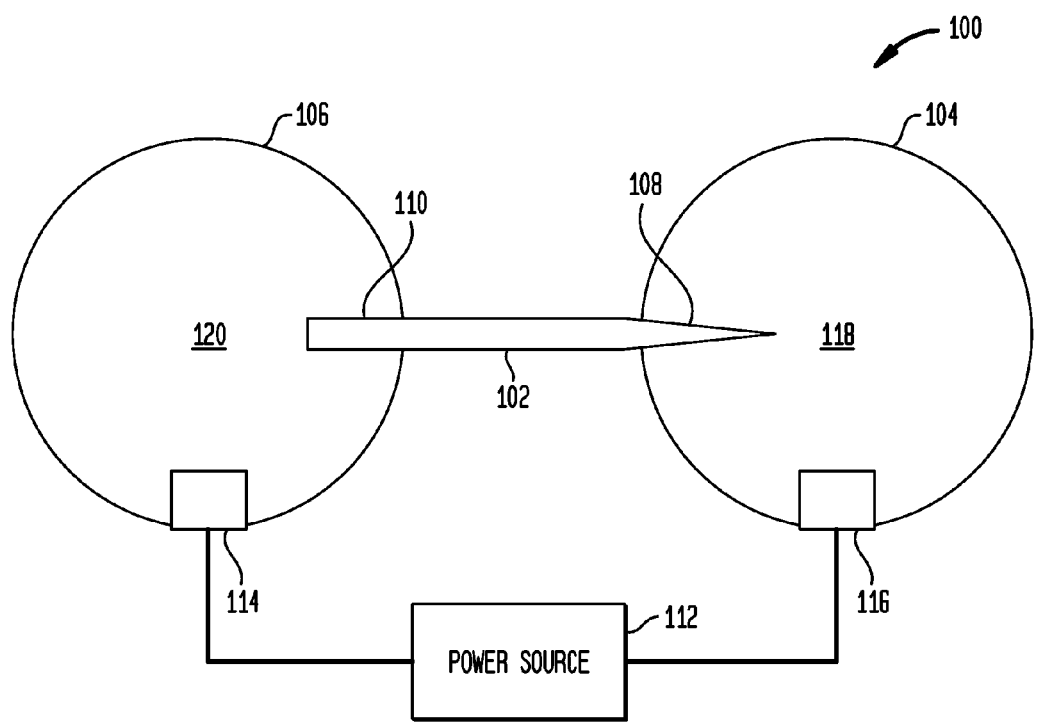
FIG. 1 depicts an embodiment of a nanopipette biosensor.

FIG. 1 illustrates a biosensor 100 that provides a high-sensitivity, low-cost, and high-speed solution for detection of a very small amount of target molecules 608 within a sample solution 118. As shown, the illustrated biosensor 100 includes a nanopipette 102 connecting a sample reservoir 104 that contains a sample solution 118 and base reservoir 106 holding a nanocolloid solution 120. In embodiments, the nanopipette is tapered at one end. As illustrated in an embodiment, the end of the nanopipette 102 connected to the sample reservoir 104, referred to as the tip end 108, is generally conic in shape. In other embodiments, the end of the nanopipette 102 that connects with the sample reservoir 104 tapers, such that the tip end 108 is reduced in diameter as compared to the general diameter of the nanopipette 102.

The nanocolloid solution 120 includes functionalized nanoparticles 200 in a buffer liquid. In embodiments, the nanocolloid nanoparticles are metal atomic particles, including, but not limited to, gold, platinum and silver. The terms "nanocolloids" and "nanocolloid nanoparticles" are used interchangeably herein and mean the nanoparticles introduced via the nanocolloid solution 120. The term "functionalized nanoparticles" refers to nanocolloids nanoparticles with attached probes specific to a particular target molecule 608. The buffer liquid can include substances such as water or a phosphate or additional particles that facilitate the detection process. In embodiments, the biosensor 100 requires as little as 10 to 100 microliters each of the sample solution 118 and the nanocolloid solution 120 for the detection process.

Figure 2A:
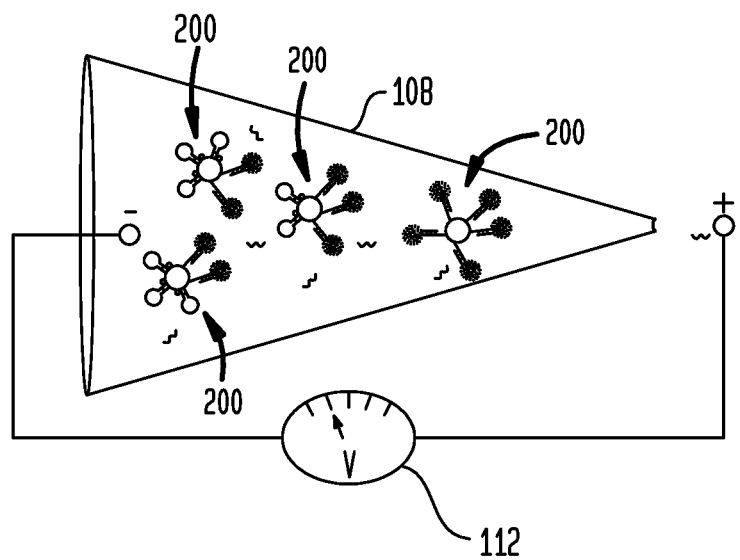
FIG. 2A depicts functionalized nanoparticles in an embodiment of a nanopipette.
Figure 2B:
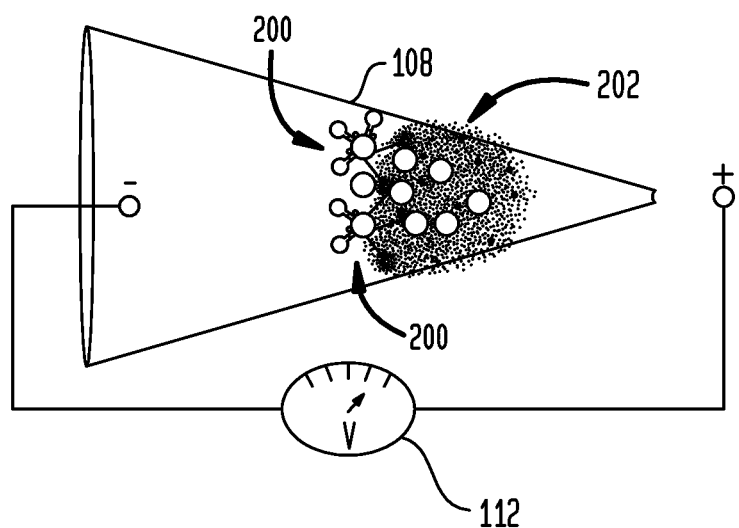
FIG. 2B depicts formation of an aggregate in an embodiment of a nanopipette.

During the detection process, a nanocolloid aggregate 202, illustrated in FIG. 2B, is formed from the nanocolloid solution 120 and the sample solution 118 within the tip end 108 of the nanopipette 102 through the application of an electric field and electrophoresis. By adjusting the original nanocolloid solution concentration, the number of functionalized nanoparticles 200 in the aggregate 202 can be tuned from 1 to 1 million, depending on how many captured target molecules 608 are desired. In embodiments, the aggregate 202 is formed from both the target molecules 608 from the sample solution 118 and the functionalized nanoparticles 200, illustrated in FIGS. 2A and 2B. The probes 602 of the functionalized nanoparticles 200 are hybridized to the target molecules 608 in the aggregate 202, activating reporters 604 associated with the probes 602.

Figure 3:
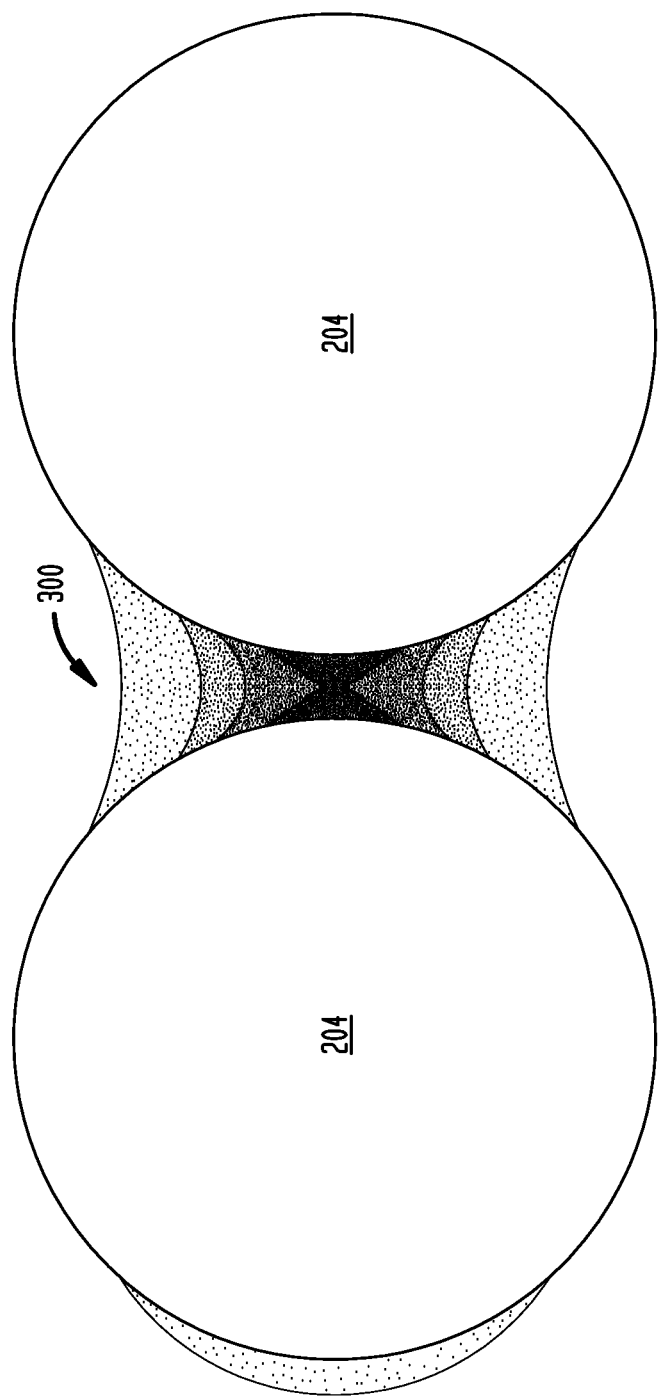
FIG. 3 depicts plasmonic hotspot formation in an aggregate.

The packing of the functionalized nanoparticles 200 within the aggregate 202 is such that the plasmonic waves of the nanocolloid nanoparticles 204 overlap, forming a plasmonic hotspot 300, shown in FIG. 3, within the aggregate 202. The aggregate 202 is small enough to include a small number of target molecules 608 packed within the separation between the nanocolloid nanoparticles 204, such that the target molecules 608 are positioned proximate to the plasmonic hotspots 300. The intensity of the hotspot 300 facilitates detection of the activated reporters 604 using optical detection methods with low-cost testing equipment. In embodiments, the plasmonic hotspots 300 are magnified even by inexpensive, portable light sources, such that the biosensor 100 can be used to quantify target molecules 608 within the sample solution 118. In addition, the entire process of forming the aggregate 202 for detection is relatively quick. In embodiments, less than 15 minutes is required to form an aggregate 202; allowing for immediate optical testing for target molecules 608 after aggregate creation.

In another embodiment, the nanoparticle aggregate 202 is formed from the nanocolloid solution 120 within the tapered tip end 108 of the nanopipette 102 through the application of an electric field and electrophoresis. The aggregate 292 is formed primarily or solely from the functionalized nanoparticles 200, where the geometry of the aggregate 202 is controlled via the application of the electric current. After formation of the aggregate 202, the sample solution 118 is drawn through the nanopipette 102 and the tip end 108 via electrophoresis, resulting in the target molecules 608 hybridizing with the probes 602 of the functionalized nanoparticles 200 in the aggregate 202. Again, the hybridization of the probes 602 activates the reporters 604, where the reporter signal is intensified by the plasmonic hotspots 300.

In some embodiments, the target molecules are labeled with fluorescent, Raman, Quantum Dots or other reporters. In such cases, unlabeled polynucleotide probes can be used and the nanocolloids nanoparticles can then be both metallic and dielectric. In these embodiments, the reporter 604 may be active prior to hybridization, but proximity to the plasmonic hotspots 300 magnifies or increases the signal strength to facilitate detection of the signal.

The speed of this technique in testing for target molecules 608 facilitates quick, portable, and inexpensive screening for various diseases. Determination of the concentration of certain types of target molecules 608, such as miRNA strands in the human body, indicates whether the levels of these strands are within normal parameters. Concentrations outside the normal parameters can signify the presence of a particular disease within a subject. Consequently, the biosensor 100 can be used to screen for conditions, including diseases (e.g., cancer, cardiovascular disease, and other diseases) and may assist a diagnostician to diagnose a subject at the subject's bedside within a matter of minutes. With the biosensor 100, doctors and other medical professionals can achieve a correct diagnosis quickly and inexpensively, facilitating rapid treatment of subjects and reducing or eliminating the need for more expensive, lengthy, and potentially inaccessible laboratory testing. The biosensor 100 can also be used to monitor the progress of treatment of a subject, facilitating adjustment of the treatment program to maximize the benefit to the subject, as well as for screening subjects for potential recurrence of a condition or disease after completion of treatment.

In other embodiments, a simple and rapid miRNA array biosensor 100 would allow for broad distribution of this molecular diagnostic device capable of diagnosing cancer and other conditions and diseases. Potentially, the biosensor 100 could be made available for home prescreening of many conditions and diseases.

Referring once again to FIG. 1, an embodiment of the biosensor 100 is shown, including the nanopipette 102 with base end 110 and tip end 108. As shown, in embodiments, the tip end 108 is tapered. In some embodiments, the tip end 108 is generally conic in shape. In embodiments, the nanopipette 102 is formed from hollow quartz or silica capillary and has an inner diameter in a range of about 1 nm to about 200 nm. In certain embodiments, the inner diameter of the tip end 108 is from about 1 nm to about 150 nm. In a particular embodiment, the inner diameter of the nanopipette 102 is approximately 111 nm, and has a cone angle of 7.3 degrees at the tip end 108.

In embodiments, the nanopipette 102 can be fabricated with a simple laser-assisted drawing technique. Suitable techniques for creating the nanopipette 102 and tip end 108 include, but are not limited to, laser-assisted drawing and ion-etching. Reactive ion-etching of the tip end 108 can result in creation of a smaller diameter nanopipette 102 and allow for formation of smaller aggregates, which can facilitate greater precision in detection of target molecules 608. Nanopipettes 102 with tip ends 108 fabricated with ion-track etching, bombardment of polymer membranes with synchrotron accelerated ions, can produce diameters as small as 2 nm for aggregation of as few as 2 or 3 functionalized nanoparticles 200.

As shown, the base reservoir 106 is located at a base end 110 of the nanopipette 102. A sample reservoir 104 is located at the tip end 108 of the nanopipette 102, such that the base reservoir 106 and sample reservoir 104 are connected via the nanopipette 102. A power source 112 capable of producing a direct current (DC) field is connected to a first electrode 114 connected to the base reservoir 106 in electrical contact with the nanocolloid solution 120 and a second electrode 116 connected to the sample reservoir 104 in electric contact with the sample solution 118.

To begin the target molecule detection process, the nanocolloid solution 120 and sample solution 118 are added to the base and sample reservoirs 104, 106, respectively. In embodiments, the nanocolloid solution 120 comprises functionalized nanoparticles 200, where the functionalized nanoparticles 200 are suspended in a buffer solution. The nanocolloids nanoparticles 200 can be metallic and include, but are not limited to, gold, platinum, and silver particles. In other embodiments, the nanocolloid nanoparticles 204 are dielectric particles. The functionalized nanoparticles 200 include attached probes 602 specific to the particular target molecules 608, and can incorporate reporters 604. In embodiments, the reporters 604 are activated by hybridization of the probes 602 by the target molecules 608. The reporters 604 can include, but are not limited to, fluorescent, Raman, and Quantum Dots reporters. In embodiments, the ionic strength of the nanocolloid solution 120 is near to that of de-ionized water, which reduces the likelihood of nanocolloid aggregation before an electric field is applied to the reservoirs 104, 106.

In an embodiment, the nanocolloid solution 120 is inserted into the base reservoir 106 before the sample solution 118 is added to the sample reservoir 104 so that the nanopipette 102 fills with the nanocolloid solution 120 through methods including, but not limited to, capillary action or electrophoresis. After the nanocolloid solution 120 is inserted in the base reservoir 106 and drawn into the nanopipette 102, the sample solution 118, potentially containing target molecules 608, is inserted into the sample reservoir 104. In embodiments, the sample solution 118 has a higher ionic strength than the nanocolloid solution 120. This difference in ionic strength will facilitate loading of the target molecules 608 into the nanopipette 102 through electrophoresis or electro-osmosis, while retaining the nanocolloid particles 200 already inserted into the nanopipette 102.

Turning now to FIGS. 2A and 2B, an embodiment of the tip end 108 of the nanopipette 102 is depicted during the target molecule detection process. Once the nanocolloid solution 120 and sample solution 118 are inserted into the biosensor 100, a first current is then run through both electrodes 114, 116 in a direction to electrophoretically drive the target molecules 608 within the sample solution 118 into the nanopipette 102, as shown in FIG. 2A. As shown, the target molecules 608 hybridize with the functionalized nanoparticles 200. The hybridized functionalized nanoparticles 200 are shown and described in more detail with respect to FIGS. 6 and 7 below.

The time to load the target molecules 608 into the nanopipette 102, referred to as the "loading time," can vary depending on the concentration of the target molecules 608 and the sensitivity required for detection of the desired target molecule 608. In certain embodiments, the initial field is run for a loading time of about 5 minutes to about 20 minutes. In other embodiments, the initial field is run for a loading time of approximately 15 minutes. In yet other embodiments, the initial field is run for loading time of approximately 10 to 15 minutes. In an embodiment, the initial field strength is generally less than or equal to 0.1 V/cm.

After completion of the loading time, the first field is no longer applied, and a second electric field of opposite polarity is applied to the biosensor 100 via the electrodes 114, 116 connected to the base reservoir 106 and the sample reservoir 104. In embodiments, this second field has a strength of about 1 V/cm. This second field causes the functionalized nanoparticles 200 and target molecules 608 to aggregate inside the tip end 108 of the nanopipette 102, as shown in FIG. 2B. In the resulting aggregate 202, the target molecules 608 are positioned between the functionalized nanoparticles 200.

The tapered shape of the tip end 108 of the nanopipette 102 focuses the electric field into sufficiently high intensity to enable nanoparticle aggregation. Because the field is strongest at the tip end 108 due to the field focusing, the aggregate 202 is confined to a small volume at the tip end 108 of the nanopipette 102. In embodiments, the high electric field at the tip end 108 allows for rapid assembly of functionalized nanoparticles 200 by induced-dipole-induced-dipole interaction. In embodiments, non-specifically bound molecules are removed from the tip end 108 due to hydrodynamic shear and drag occurring from the electro-osmotic flow in the nanopipette 102, removing nanoparticles, target molecules, and/or extraneous material in the sample solution 118 that are not of concern in the detection process from the nanopipette 102. The result is an aggregate 202 located at a predictable location in the tip end 108 and a reduced quantity of non-specifically bound or non-target molecules 608 interfering in the detection process.

In embodiments, the resulting aggregate 202 is approximately one micron or less in each dimension, meaning that in this instance there are approximately 100 functionalized nanoparticles 200 within the aggregate 202, with target molecules 608 positioned between the contact points of nanocolloid nanoparticles 204. In an embodiment, the second field places the target molecules 608 in about 10 nm spaces between the nanocolloid nanoparticles 204. This spacing or gap between nanocolloid nanoparticles 204 can be adjusted by changing the voltage on the second field: If the voltage is increased, the spacing or gap between the nanocolloid nanoparticles 204 will be decreased in size. Conversely, decreasing the voltage will increasing the size of the gap or spacing between the nanocolloid nanoparticles 204. This spacing, as well as the spherical geometry of the nanocolloid nanoparticles 204, allows the plasmonic waves of the different nanocolloid nanoparticles 204 to overlap and form highly intense plasmonic hotspots 300.

In other embodiments, the functionalized nanoparticles 200 are packed into the aggregate 202 at the tip end 108 and then the target molecules 608 are drawn through the aggregate 202 and the tip end 108. Here, the nanocolloid solution 120 is drawn into the nanopipette 102, whether through electrophoresis or capillary action. An electric current is applied to pack the functionalized nanoparticles 200 into an aggregate 202 located at the tip end 108, where the geometry of the aggregate 202 is controlled by the applied electric current. This first current is stopped, the sample solution 118 introduced and a second, reverse voltage applied to drive the sample solution target molecules 608 into the nanopipette 102 and through the aggregate 202. As the sample solution 118 transits through the aggregate 202, the target molecules 608 will be captured by the probes of the functionalized nanoparticles 200 within the aggregate 202.

FIG. 3 shows the packing of the nanocolloid nanoparticles 204 to form a plasmonic hotspot 300. Intense plasmonic hotspots 300 can be generated when two nanocolloids nanoparticles 204 are in near contact, but with a separation greater than the electron tunneling length of a few nanometers. The plasmonic hotspots 300 develop when the spacing or gap between the contact points of the nanocolloids nanoparticles is within a certain range, for example between approximately 4 nanometers and 20 nanometers. Typically, such nanogaps with an appropriate symmetry and structure to trap bulk light are difficult to fabricate. In the described biosensor 100, the geometry of the nanocolloid aggregate 202 or spacing of the nanocolloids 204 is controlled to facilitate the creation of plasmonic hotspots 300. In this technique, the electric field applied by the electrodes 114, 116 is capable of adjusting the spacing to its optimum value for any given aggregate 202 to optimize the intensity of the plasmonic hotspot 300. In embodiments, the distance between the closest points of the nanocolloid nanoparticles 204 is approximately 10 nm.

As indicated, plasmonic waves resonate from each nanocolloid nanoparticle 204. Where the nanocolloid nanoparticles 204 are closest to each other, these plasmonic waves overlap, forming the hotspot 300. As the distance between the nanocolloids nanoparticles 200 increases, such as above and below the contact points the nanocolloids nanoparticles, the plasmonic waves do not resonate as well, and the heat formed from the resonance decreases. In a given aggregate 202, there can be numerous nanocolloid nanoparticles 204 forming a multiple plasmonic hotspots 300. The plasmonic hotspots 300 from all of the interactions between the nanocolloid nanoparticles 204 facilitate creation of an optical image that is readable using readily available optical detection methods. For example, where the nanocolloid nanoparticles 204 are functionalized with probes 602 including fluorescent reporters 604, and where the reporter 604 is activated by hybridization of the probes 602 by the target molecule 608, the fluorescent signal from the reporter 604 indicates the presence of the target molecule 608. This fluorescent signal is intensified by the plasmonic hotspot 300 facilitating optical detection.

Figure 4:
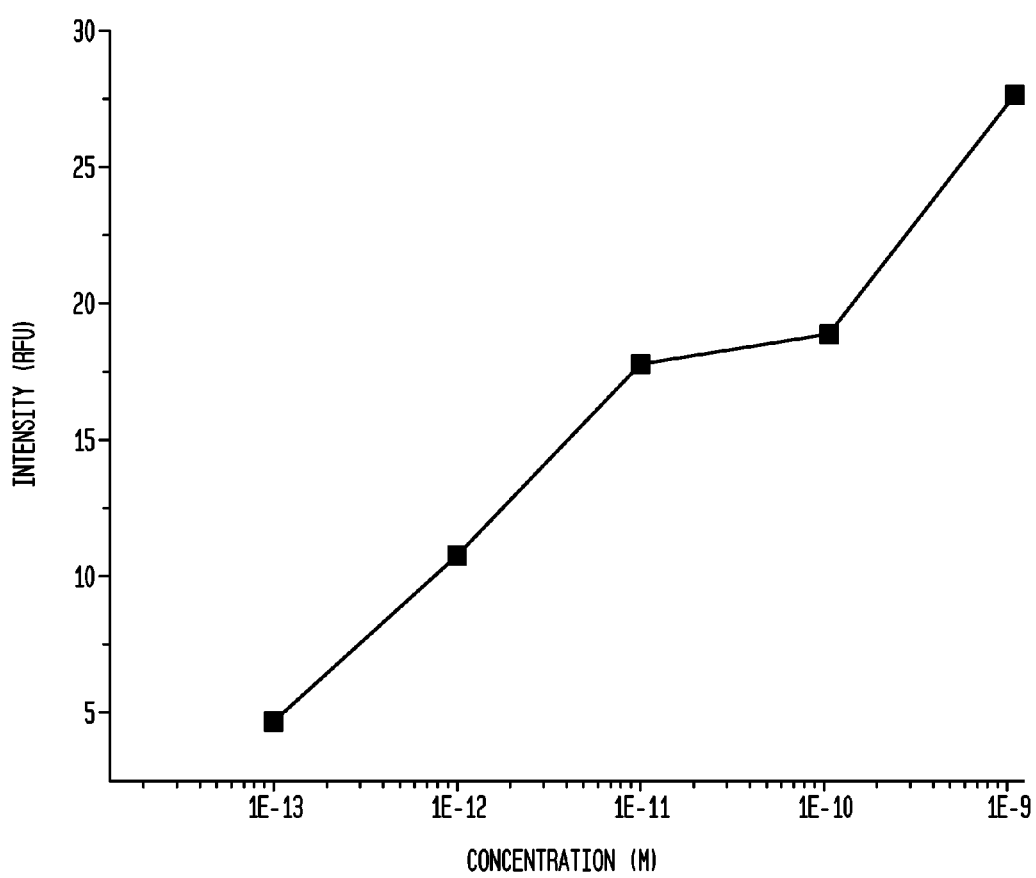
FIG. 4 depicts observed correlation in increasing intensity of plasmonic hotspots detected from an embodiment of a nanopipette biosensor in relation to concentration of target molecules.

As shown in FIG. 4, the amount of target molecules 608 in the sample solution 118 is directly proportional to the intensity of fluorescent reporters 604. Here, molar concentration of target molecules 608 is shown on the x-axis, while the y-axis denotes intensity of the fluorescent reporters 604 observed in relative fluorescence units ("RFU"). To calibrate the nanopipette biosensor 100, the biosensor 100 can be used with a sample solution 118 containing a known number of target molecules 608 and a nanocolloid solution 120 containing a known number of nanocolloid nanoparticles 204. Repeated tests with varying numbers of target molecules 608 and nanocolloid nanoparticles 204 permit quantification of target molecules 608 based upon intensity of the detected signals from the reporters 604.

In embodiments, the biosensor 100 is able to quantify a large number of target molecules 608 at low concentrations within the sample solution 118. For example, embodiments can detect concentrations of a particular target molecule 608 into the sub-femtoM range or less than 100 copies within a microliter of sample solution 118. This embodiment can be used with various optical detection methods, including Raman, Surface Enhanced Raman Spectroscopy ("SERS"), Fluorescence Resonance Energy Transfer ("FRET"), and absorption.

Figure 5:
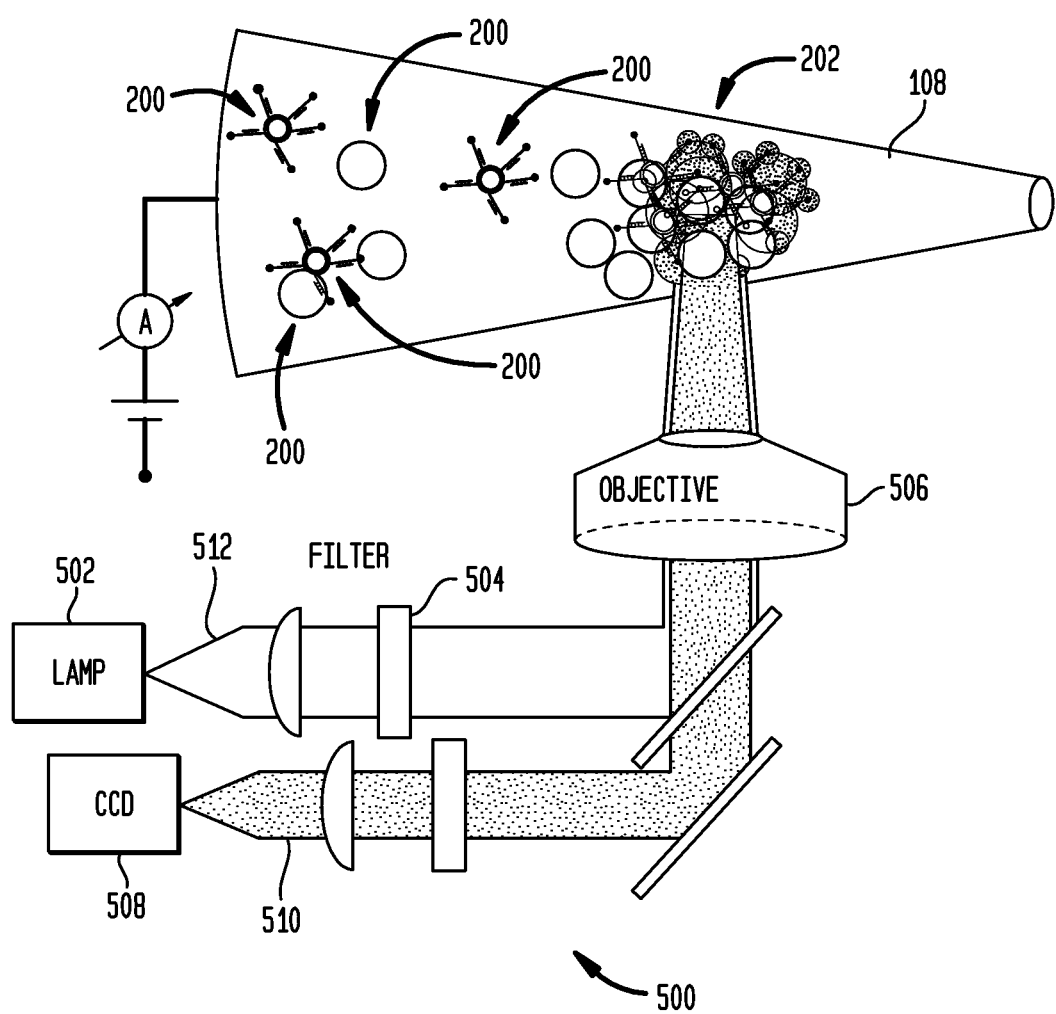
FIG. 5 depicts a cross-section of a nanopipette within an embodiment of the nanopipette biosensor incorporating an embodiment of an optical detection system.

As illustrated in FIG. 5, a simple optical detection system 500 is shown. A light source 502, such as a lamp or light-emitting diode (LED), emitting visible light 512 directed toward the aggregate 202 through a filter 504 and an objective lens 506. In embodiments, the light source 502 is an inexpensive source that emits low-intensity bulk light 512. The visible light 512 illuminates the aggregate 202, formed from functionalized nanoparticles 200, some or all of which are hybridized with target molecules 608. Signals from reporters 604 activated by the presence of the target molecules 608 are magnified by the plasmonic hotspots 300 resulting in a signal 510 detectable through an optical sensor 508 such as a charge-coupled device camera ("CCD"). In embodiments, the light signal 510 is directed through the lens 506 and can be filtered before being received by the optical sensor 508. In other embodiments, the optical sensor 508 is an inexpensive optical camera.

Figure 6:
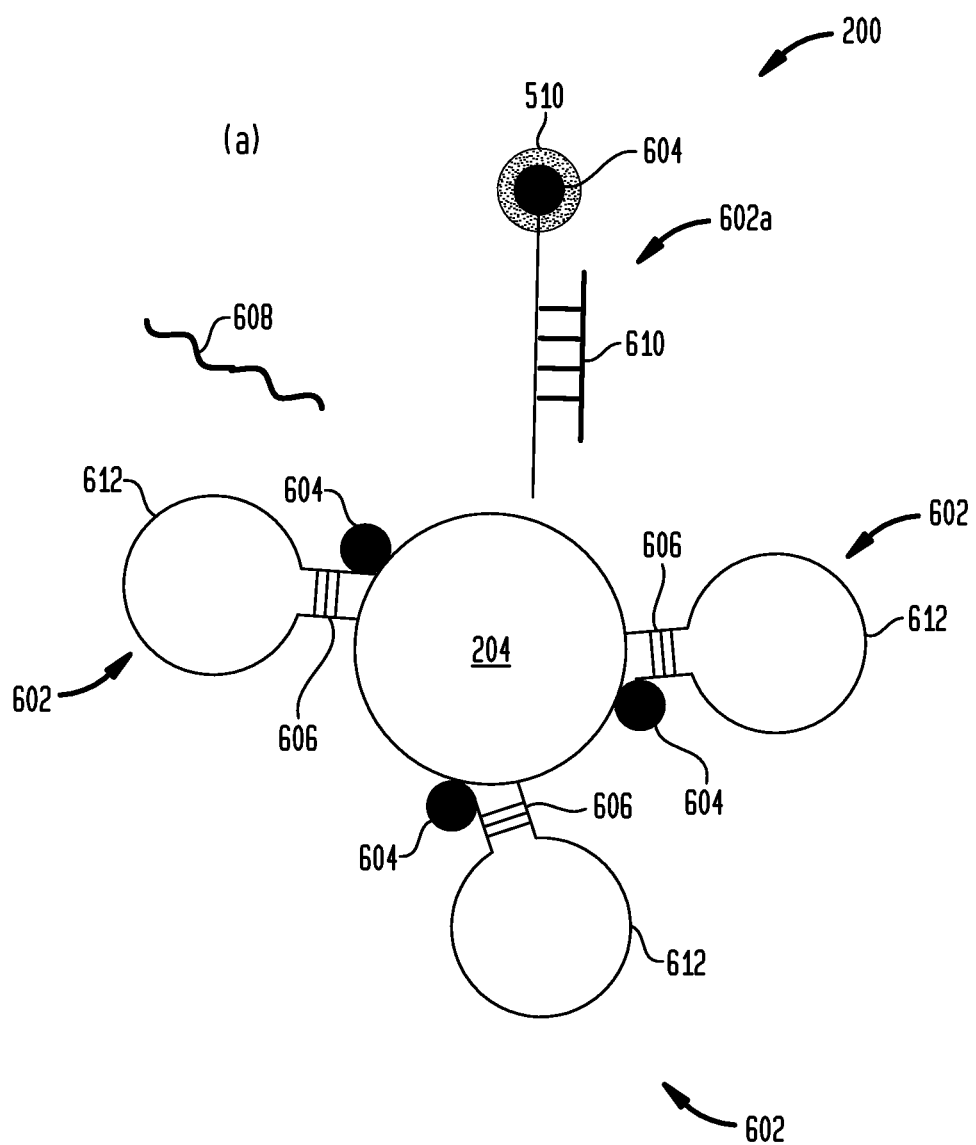
FIG. 6 depicts an embodiment of a functionalized nanoparticle in a nanocolloid solution.

Referring now to FIG. 6, in another embodiment, the biosensor 100 uses functionalized nanoparticles 200 with probes 602 including FRET reporters 604 for label-free detection of the target molecules 608. As illustrated, hairpin polynucleotide probes 602 with reporters 604, such as end-tagged fluorophores, are attached to nanocolloid nanoparticles 204 within a nanocolloid solution 120. Prior to hybridization, the hairpin probes' fluorophores 604 are quenched by the nanocolloid nanoparticles 204, such as metallic or dielectric nanoparticles, and do not emit a readable optical signal while proximate to the nanocolloid nanoparticles 204.

Figure 7:
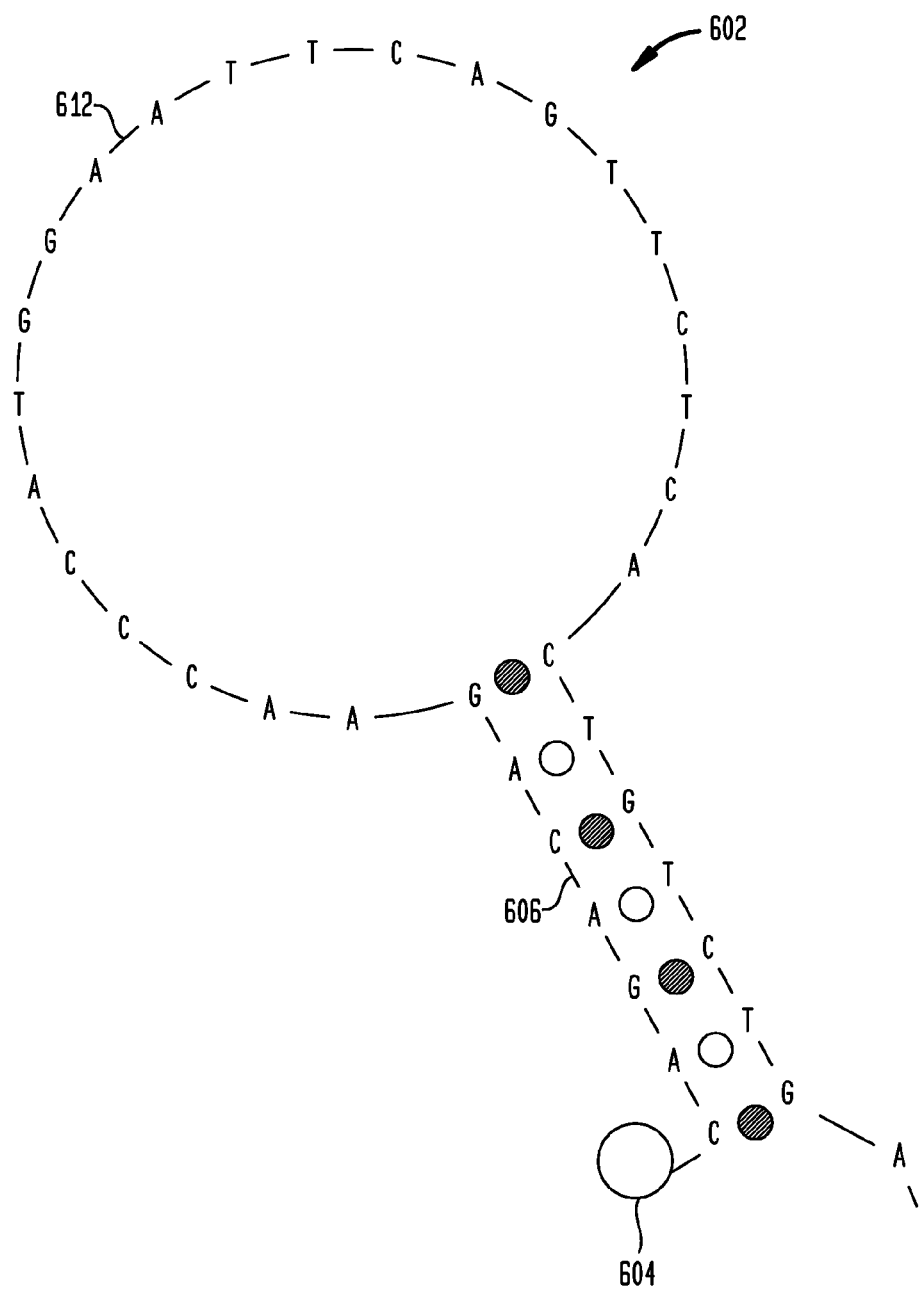
FIG. 7 depicts an embodiment (SEQ ID NO. 2) of a hairpin polynucleotide probe.

As shown in FIGS. 6 and 7, in an embodiment, the hairpin probe of SEQ ID NO: 2 602 is formed from double-stranded DNA ("dsDNA") 606 and single-stranded DNA of SEQ ID NO: 1 ("ssDNA") 612, where the ssDNA 612 is complementary to the miRNA sequence of the desired target molecule 608. In an embodiment, the dsDNA serves as a stem 606 of the hairpin probe 602 and the ssDNA forms the loop 612 of the hairpin probe 602. The probe 602 can be formed from any polynucleotide capable of binding to the desired miRNA target. Such polynucleotides include polyncoeotides comprising wholly naturally-occurring nucleotides and wholly non-naturally occurring polynucleotides; and polynucleotides comprising both naturally-occurring and non-naturally occurring nucleotides. Polynucleotides appropriate for use in the probes of this disclosure include but are not limited to DNA, RNA, and LNA. In the embodiment shown in FIG. 7, the DNA sequence of the hairpin probe 602 is 5'cagacagaacccatggaattcagttctcactgtctga3' (SEQ ID NO. 2). This arrangement results in a highly selective biosensor 100 able to detect low concentrations of a target molecule 608 miRNA out of all the possible miRNAs with similar sequences over 22 bases and large variations in expression level (as much as 100 fold). In the embodiment illustrated in FIG. 7, the ssDNA loop 612 is complementary to a biomarker for oral cancer, human miR-146a 5'UGAGAACUGAAUUCCAUGGGUU3' (SEQ ID NO. 1). This embodiment does not require the nanocolloid solution 120 to have an ionic strength similar to de-ionized water, as the dsDNA that forms the probe stem 606 prevents aggregation in high ionic strength nanocolloid solutions 120 prior to electrophoresis in the biosensor 100. In embodiments, the nanocolloid solution 120 is packed into the nanopipette 102 by applying a positive voltage of 1 V/cm for a period of approximately fifteen minutes.

The sample solution 118 is then placed into the sample reservoir 104, and a current of −1 V/cm is run on the biosensor 100, driving the target molecules 608 into the nanopipette 102. During this process, the target molecules 608 become trapped within the nanopipette 102 and hybridize with the complementary ssDNA loop 612 of the hairpin probes 602. The hybridization releases the fluorophores 604 attached to the hairpin probes 602. As shown, the target molecule 608 and complementary ssDNA loop 612 form a DNA-RNA hybrid 610, linearizing the hairpin shape of the probe 602. The linearized hairpin probe 602a is shown in FIG. 6, emitting a signal 510. Consequently, the distance between the fluorophores 604 and the nanocolloid nanoparticle 204 increases such that the quenching of the fluorophores 604 is reduced or eliminated. However, the fluorescent signal 510 from the fluorophores 604 is still too weak to be detected using readily available optical methods.

A reverse voltage of +1 V/cm is then applied by the power source 112 to pack the functionalized nanoparticles 200 to the tip end 108 of the nanopipette 102 and form the aggregate 202. Light 512 from light source 502 is directed toward the aggregate 202, which produces a fluorescent signal 510 from the now activated reporters 604. The combined fluorescent signal 510 from the reporters 604 on hybridized hairpin probes 602 within the aggregate 202 becomes strong enough through the magnification or intensification caused by the plasmonic hotspots 300 to be detected with inexpensive optical cameras 508.

In another embodiment, first the nanocolloid nanoparticles 204 with hairpin probes 602 and end-tagged reporters 604 are packed into the aggregate 202 and then the target molecules 608 are drawn through the aggregate 202 and the tip end 108. As the sample solution transits through the aggregate 202, the target molecules 608 miRNA will hybridize with the complementary ssDNA loop 612 of the hairpin probes 602.

In embodiments, the reservoirs 118, 120 and nanopipette 102 are housed in or on a microfluidic chip. In other embodiments, multiple individual biosensor 100 are arranged in a parallel array or other geometries, allowing for the testing for concentrations of multiple target molecules 608 in different nanopipettes 102 within one run of the biosensor 100. In other embodiments, multiple nanopipettes 102 and multiple base reservoirs 106 are arranged around a single sample reservoir 104, allowing the biosensor 100 to run tests to detect different target molecules 608 in one iteration. In this embodiment, the sample reservoir 104 is loaded with sufficient sample solution 118 to allow for the detection of multiple target molecules 608.

What has been described above includes examples of aspects of the claimed subject matter. It is, of course, not possible to describe every conceivable combination of components or methodologies for purposes of describing the claimed subject matter, but one of ordinary skill in the art may recognize that many further combinations and permutations of the disclosed subject matter are possible. Accordingly, the disclosed subject matter is intended to embrace all such alterations, modifications and variations that fall within the spirit and scope of the appended claims. Furthermore, to the extent that the terms "includes," "has" or "having" or variations in form thereof are used in either the detailed description or the claims, such terms are intended to be inclusive in a manner similar to the term "comprising" as "comprising" is interpreted when employed as a transitional word in a claim.

What is claimed is:

1. A method for detecting a target nucleic acid molecule in a sample solution, comprising:
   providing a biosensor comprising a base reservoir, a sample reservoir and a nanopipette that connects the base reservoir and the sample reservoir, wherein the nanopipette includes a tapered tip end;
   adding a nanocolloid solution comprising functionalized nanoparticles to the base reservoir, wherein each of the functionalized nanoparticles comprises a nanocolloid nanoparticle, a probe complementary to the target molecule, and a reporter;
   loading the nanocolloid solution into the nanopipette;
   adding the sample solution to the sample reservoir;
   loading the sample solution into the nanopipette where the target molecule in the sample solution hybridizes to the probe of at least one of the functionalized nanoparticles, thereby activating the reporter;
   assembling an aggregate of the functionalized nanoparticles, wherein the aggregate assembles proximate to the tip end of the nanopipette;
   developing a plasmonic hotspot based at least in part upon control of spacing of the functionalized nanoparticles in the aggregate;
   increasing an intensity of a signal produced by the activated reporter through proximity of the activated reporter and the plasmonic hotspot; and
   observing the signal produced by the activated reporter using an optical detection technique wherein an amount of the target nucleic acid is directly proportional to the signal produced by the activated reporter.

2. The method of claim 1, wherein the steps of loading the sample solution into the nanopipette and assembling the aggregate comprise:
   applying a first voltage to the sample reservoir and the base reservoir, wherein a current from the first voltage drives the sample solution into the nanopipette; and applying a second voltage to the sample reservoir and the base reservoir, the second voltage having a reverse polarity from the first voltage, wherein the functionalized nanoparticles form the aggregate proximate to the tip end of the nanopipette based at least in part upon the application of the second voltage.

3. The method of claim 2, further comprising selecting the second voltage to control the spacing of the functionalized nanoparticles within the aggregate.

4. The method of claim 3, wherein the second voltage is selected to control the spacing to approximately 4 to 20 nanometers between contact points of the functionalized nanoparticles within the aggregate.

5. The method of claim 1, wherein the target molecule is positioned proximate to the plasmonic hotspot within the aggregate.

6. The method of claim 1, wherein the optical detection technique is SERS, Raman, FRET, or absorption.

7. The method of claim 1, wherein the probe is a hairpin polynucleotide probe.

8. The method of claim 7, wherein the reporter is a flourophore and wherein the hairpin polynucleotide probe comprises a single-stranded DNA loop complementary to microRNA of the target molecule, wherein the flourophore is quenched by the nanocolloid nanoparticle prior to hybridization of the target molecule.

9. The method of claim 8, wherein hybridization of the target molecule comprises hybridizing the single-stranded DNA loop of the hairpin probe and the microRNA sequence of the target molecule, thereby linearizing the hairpin probe and eliminating the quenching of the flourophore by the nanocolloid nanoparticle, wherein the signal is a fluorescent signal emitted by the flourophore.

10. The method of claim 9, wherein the fluorescent signal is intensified by the plasmonic hotspot of the aggregate.

11. The method of claim 1, further comprising quantifying presence of the target molecule within the sample solution based upon observed intensity of the signal.

12. The method of claim 1, wherein the tip end of the nanopipette has a diameter of less than or equal to 100 nm.

13. The method of claim 1, wherein the reporter is a quantum dot.

14. A method for detecting a target nucleic acid molecule in a sample solution, comprising:
providing a biosensor comprising a base reservoir, a sample reservoir and a nanopipette that connects the base reservoir and the sample reservoir, wherein the nanopipette includes a tapered end connected to the sample reservoir;
adding a nanocolloid solution comprising functionalized nanoparticles to the base reservoir, wherein each of the functionalized nanoparticles comprises a nanocolloid nanoparticle, a probe complementary to the target molecule, and a reporter;
loading the nanocolloid solution into the nanopipette;
assembling an aggregate formed from the functionalized nanoparticles, wherein the aggregate is assembled proximate to the tip end of the nanopipette;
developing a plasmonic hotspot based at least in part upon control of spacing of the functionalized nanoparticles in the aggregate;
adding the sample solution to the sample reservoir;
loading the sample solution into the nanopipette such that the target molecule in the sample solution transits the aggregate and is hybridized by the probe of at least one of the functionalized nanoparticles, activating the reporter;
increasing intensity of the activated reporter based upon a proximity of the activated reporter and the plasmonic hotspot; and
detecting the activated reporter using an optical detection technique, wherein an amount of the target nucleic acid molecule is directly proportional to the signal produced by the activated reporter.

15. The method of claim 14, wherein the step of detecting the activated reporter comprises observing a signal emitted by the activated reporter, where the signal is intensified by the plasmonic hotspot.

16. The method of claim 14, wherein the steps of assembling the aggregate comprise and loading the sample solution into the nanopipette comprise:
applying a first voltage to the sample reservoir and the base reservoir, such that the functionalized nanoparticles form the aggregate proximate to the tip end of the nanopipette; and
applying a second voltage to the sample reservoir and the base reservoir, the second voltage having a reverse polarity from the first voltage, wherein a current from the second voltage drives the sample solution into the nanopipette such that the target molecule transits the aggregate.

17. The method of claim 16, further comprising selecting the first voltage to control a gap between contact points of the nanocolloid nanoparticle of the functionalized nanoparticles within the aggregate to optimize intensity of the plasmonic hotspot.

18. The method of claim 17, the gap between contact points of the nanocolloid nanoparticle of the functionalized nanoparticles within the aggregate is approximately 10 nanometers.

19. The method of claim 14, wherein the reporter is a fluorophore and the probe is a hairpin polynucleotide probe that comprises a single-stranded DNA loop complementary to microRNA of the target molecule, wherein the flourophore is quenched by the nanocolloid nanoparticle prior to hybridization of the target molecule.

20. A method for detecting a target nucleic acid molecule in a sample solution, comprising:
providing a biosensor comprising a base reservoir, a sample reservoir and a nanopipette that connects the base reservoir and the sample reservoir, wherein the nanopipette includes a tapered tip end;
adding a nanocolloid solution comprising functionalized nanoparticles to the base reservoir, wherein each of the functionalized nanoparticles comprises a nanocolloid nanoparticle and a probe complementary to the target molecule;
loading the nanocolloid solution into the nanopipette;
adding the sample solution to the sample reservoir, wherein the sample solution comprises the target molecule labeled with a reporter;
applying a first voltage to the sample reservoir and the base reservoir, wherein the sample solution is loaded into the nanopipette based at least in part upon application of the first voltage, where the target molecule in the sample solution hybridizes to the probe of at least one of the functionalized nanoparticles;
assembling an aggregate of the functionalized nanoparticles by applying a second voltage to the sample reservoir and the base reservoir, the second voltage having a reverse polarity from the first voltage, wherein the aggregate assembles proximate to the tip end of the nanopipette;

developing a plasmonic hotspot based at least in part upon control of spacing of the functionalized nanoparticles in the aggregate; and increasing an intensity of a signal produced by the reporter through proximity of the reporter and the plasmonic hotspot; and observing the signal produced by the reporter using an optical detection technique based at least in part upon the increased intensity of the signal wherein an amount of the target nucleic acid is directly proportional to the signal produced by the reporter.

* * * * *

```
                       SEQUENCE LISTING

<160> NUMBER OF SEQ ID NOS: 2

<210> SEQ ID NO 1
<211> LENGTH: 22
<212> TYPE: RNA
<213> ORGANISM: Homo sapiens

<400> SEQUENCE: 1
ugagaacuga auuccaugggg uu                                          22

<210> SEQ ID NO 2
<211> LENGTH: 37
<212> TYPE: DNA
<213> ORGANISM: Artificial Sequence
<220> FEATURE:
<223> OTHER INFORMATION: rcomprises reverse complement of human miR146-a

<400> SEQUENCE: 2
cagacagaac ccatggaatt cagttctcac tgtctga                           37
```